US005994500A

United States Patent [19]
Drucker et al.

[11] Patent Number: 5,994,500
[45] Date of Patent: *Nov. 30, 1999

[54] ANTAGONISTS OF INTESTINOTROPHIC GLP-2 PEPTIDES

[75] Inventors: Daniel J. Drucker; Anna E. Crivici, both of Toronto; Martin Sumner-Smith, Bolton, all of Canada

[73] Assignee: 1149336 Ontario Inc., Toronto, Canada

[*] Notice: This patent is subject to a terminal disclaimer.

[21] Appl. No.: 08/683,890

[22] Filed: Jul. 19, 1996

[51] Int. Cl.$^6$ ...................................................... C07K 5/00
[52] U.S. Cl. ............................ 530/324; 514/12; 530/308; 530/324; 435/71.1; 435/325; 435/69.1
[58] Field of Search ................................... 514/12–13, 3, 514/4; 530/303, 308, 324–326; 435/325, 320.1, 69.1, 69.4, 71.1

[56] References Cited

FOREIGN PATENT DOCUMENTS 612531   8/1994   European Pat. Off. .

OTHER PUBLICATIONS

Barragan, J.M.; Rodriguez, R.E.; and Blazquez, E. Changes in arterial blood pressure and heart rate induced by glucagon–like peptide–1–(7–36)amide in rats. *American Journal of Physiology.* 266 (3 Pt 1), pE459–66, Mar. 1994.

Bloom, S.R. Gut Hormones in adaptation. *Gut.* 28, S1, pp. 31–35, 1987.

Brubaker, Patricia L. Regulation of Intestinal Proglucagon–Derived Peptide Secretion by Intestinal Regulatory Peptides. *Endocrinology.* vol. 128, No. 6, pp. 3175–3182, 1991.

Buhl, Thora; Thim, Lars; Kofod, Hans; Orskov, Catherine; Harling, Henrik; and Holst, Jens J. Naturally Occurring Products of Proglucagon 111–160 in the Porcine and Human Small Intestine. *The Journal of Biological Chemistry.* vol. 263, No. 18, pp. 8621–8624, Issue of Jun. 25, 1988.

Calvo, J.C.; Yusta, B; Mora, F; and Blazquez, E. Structural characterization by affinity cross–linking of glucagon–like peptide–1 (7–36) amide receptor in rat brain. *J. Neurochem.* 64(1), pp. 299–306, Jan. 1995.

Cheeseman, Chris I.; and Raymand Tsang. The effect of gastric inhibitory polypeptide and glucagon like peptides on intestinal basolateral membrane hexose transport. *The American Physiological Society.* APSracts 3:0071G, Apr. 16, 1996.

Drucker, *Pancreas.* 1990, 5(4):484.

Ehrlich, Peter; Tucker, Devin; Asa, Sylvia L.; Brubacker, Patricia L.; and Drucker, Daniel J. Inhibition of pancreatic proglucagon gene expression in mice bearing subcutaneous endocrine tumors. *American Journal of Physiology.* pp. E662–E671, 1994.

Goerge, S.K.; Uttenthal, L.O.; Ghiglione, M.; and Bloom, S.R. Molecular forms of glucagon–like peptides in man. *FEBS Letters.* vol. 192, No. 2, pp. 275–278, Nov. 1985.

Hoosein, Naseema M.; and Gurnd, Ruth S. Human glucagon–like peptides 1 and 2 activate rat brain adenylate cyclase. *FEBS Letters.* vol. 178, No. 1, pp. 83–86, Dec. 1984.

Irwin, David M.; and Wong, Jaffe. Trout and Chicken Proglucagon: Alternative Splicing Generates mRNA Transcripts Encoding Glucagon–Like Peptide 2. *Molecular Endocrinology.* 9:267–277, 1995.

Lee, Ying C.; Asa, Sylvia L.; and Drucker, Daniel J. Glucagon Gene 5'–Flanking Sequences Direct Expression of Simian Virus 40 Large T Antigen to the Intestine, Producing Carcimona of the Large Bowel in Transgenic Mice. *The Journal of Biological Chemistry.* vol. 267, No. 15, pp. 10706–10708, May 25, 1992.

Lund, P. Kay; Hoyt, Eileen; Simmons, James G.; and Ulshen, Martin H. Regulation of Intestinal Glucagon Gene Expression during Adaptive Growth of Small Intestine. *Digestion.* 54:371–373. 1993.

Mojsov, Svetlana; Heinrich, Gerhard; Wilson, Ira B.; Ravazzola, Mariella; Orci, Lelio; and Habener, Joel F. Preproglucagon Gene Expression in Pancreas and Intestine Diversifies at the Level of Post–translational Processing. *The Journal of Biological Chemistry*, vol. 261, No. 25, pp. 11880—11889, Sep. 5, 1986.

Mommsen, Thomas P.; Andrews, P.C.; and Plisetskaya, Erika M. Glucagon–like peptides activate hepatic gluconeogenesis. *FEBS Letters.* vol. 219, No. 1, pp. 227–232, Jul. 1987.

Nishi and Steiner, *Mol. Endocrinol.*, 1990, 4:1192–8.

Orskov, C.; Buhl, T.; Rabenhoj, L.; Kofod, H.; and Holst, J.J.. Carboxypeptidase–B–like processing of the C–terminus of glucagon–like peptide–2 in pig and human small intestine. *FEBS Letters.* 247(2), pp. 193–196, Apr. 24, 1989.

Orskov, C.; Holst, J.J.; Pouisen, S. Seier; and Krikegaard, P. Pancreatic and intestinal processing proglucagon in man. *Diabetologia.* 30:874–881, 1987.

Orskov, C; and Holst, J.J. Radio–immunoassays for glucagon–like peptides 1 and 2 (GLP–1 and GLP–2), *Scand. J. Clin. Lab. Invest.* 47(2), pp. 165–174, Apr. 1987.

Orskov, Catherine; Holst, Jens J.; Knuhtsen, Svend; Baldissera, Furio G.A.; Poulsen, Steen S.; and Nielsen, O. Vagn. Glucagon–Like Peptides GLP–1 and GLP–2. Predicted Products of the Glucagon Gene, Are Secreted Separately from Pig Small Intestine but Not Pancreas. *Endocrinology.* vol. 119, No. 4, pp. 1467–1475, 1986.

Ruiz–Grand, C.; Pintado, J.; Alarcon, C.; Castilla, C.; Valverde, I; Lopez–Novoa, J.M. Renal catabolism of human glucagon–like peptides 1 and 2. *Can. J. Physiol. Pharmacol.* 68 (12), pp. 1568–1573, Dec. 1990.

(List continued on next page.)

*Primary Examiner*—Sheila Huff
*Attorney, Agent, or Firm*—Pennie & Edmonds LLP

[57] ABSTRACT

Antagonists of glucagon-like peptide 2, have been identified. Their effects on the growth of gastrointestinal tissue are described. Its formulation as a pharmaceutical, and its therapeutic and related uses in treating bowel tissue, are described. Also described are methods of identifying antagonists of glucagon-like peptide 2.

15 Claims, No Drawings

OTHER PUBLICATIONS

Shennan, K.I.J.; Holst, J.J.; and Docherty, K. Proglucagon expression, posttranslational processing and secretion in SV40–transformed islet cells. *Molecular and Cellular Endocrinology*. 67(1989), pp. 93–99.

Watanabe, Nobuaki; Matsuyama, Tatsuo; Namba, Mitsuyoshi; Miyagawa, Jun–ichiro; Itoh, Hidehiko; Komatsu, Ryoya; Kono, Norio; and Tarui, Seiichiro. Trophic Effect of Glucagon–(1–21)–Peptide on the Isolated Rat Ileal Mucosal Cells. *Biochemical and Biophysical Research Communications*. vol. 152, No.3, pp. 1038–1044, May 16, 1988.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 33 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

```
His Ala Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
                20                  25                  30

Asp
```

ANTAGONISTS OF INTESTINOTROPHIC GLP-2 PEPTIDES

I. FIELD OF THE INVENTION

This invention relates to glucagon-related peptides which are functional antagonists of glucagon-like peptides-2, and to their use therapeutically to counter hyperplasia or induce hypoplasia particularly in intestinal tissue.

II. BACKGROUND TO THE INVENTION

Expression of the glucagon gene yields a tissue-determined variety of peptide products that are processed from the 160 residue proglucagon product. The organization of these peptides within the proglucagon precursor was elucidated by the molecular cloning of preproglucagon cDNAs from the anglerfish, rat, hamster and bovine pancreas. These analyses revealed that preproglucagon contains not only the sequence of glucagon and glicentin, but also two additional glucagon-like peptides (GLP-1 and GLP-2) separated from glucagon and each other by two spacer or intervening peptides (IP-I and IP-II). These peptides are flanked by pairs of basic amino acids, characteristic of classic prohormone cleavage sites, suggesting they might be liberated after posttranslational processing of proglucagon (Drucker, Pancreas, 1990, 5(4):484). Analysis of the peptides liberated from proglucagon in the pancreatic islets of Langerhans, for instance, suggests the primary pancreatic peptide liberated is the 29-mer glucagon, whereas glicentin, oxyntomodulin, IP-II and the glucagon-like peptides are more prevalent in the small and large intestines. This demonstration that the glucagon-like peptides are found in the intestine has prompted research into the precise structure and putative function(s) of these newly discovered gut peptides. Most studies have focussed on GLP-1, because several lines of evidence suggested that GLP-1 may be an important new regulatory peptide. Indeed, it has been determined that GLP-1 is the most potent known peptidergic stimulus for insulin release, an action mediated in a glucose-dependent manner through interaction with receptors on pancreatic β cells. GLP-1 and its derivatives are in development for use in the treatment of diabetics.

With respect to its biological role of GLP-2, co-pending application U.S. patent application Ser. No. 08/422,540, incorporated in its entirety herein by reference, discloses that mammalian GLP-2 acts as a trophic agent, to promote growth of intestinal tissue. The effect of GLP-2 is marked particularly by increased growth of the small intestine. Furthermore, co-pending U.S. patent application Ser. No. 08/631,273, incorporated in its entirety herein by reference, discloses that analogs of vertebrate GLP-2 can have enhanced intestinotrophic activity.

III. SUMMARY OF THE INVENTION

It has now been discovered that alteration of GLP-2 peptide structure can yield peptides capable of inhibiting the intestinotrophic activity of GLP-2. More particularly, and according to one aspect of the invention, there are provided antagonists comprising an amino acid sequence corresponding to that of a first reference mammalian GLP-2 which has been mutated so that from one to four of any of the first four N-terminal residues are deleted. In another aspect of the invention, the antagonists correspond to a reference mammalian GLP-2 that has been mutated so that at least one amino acid selected from the amino acid positions corresponding to the amino acid positions of human GLP-2 at $Asp^{15}$, $Phe^{22}$, $Thr^{29}$, $Thr^{32}$ and $Asp^{33}$ is substituted with an amino acid which does not naturally occur at that position in the reference GLP-2. In still another aspect of the invention, the antagonists correspond to a reference mammalian GLP-2 mutated so that both positions $Ser^5$ and $Ser^7$ are substituted with amino acids other than Serine. In another aspect of the invention, position $Ala^2$ is substituted with an amino acid selected from the group consisting of Leu, Cys, Glu, Arg, Trp, and $PO_3$-$Tyr^2$. In yet another aspect of the invention, the antagonist corresponds to a polypeptide with any combination of the above substitutions and deletions mutated relative to the reference mammalian GLP-2.

Also provided as an aspect of the invention are methods of producing and identifying GLP-2 antagonists.

For use in medical treatment, there is further provided by the present invention a pharmaceutical composition comprising an amount of a GLP-2 antagonist effective to antagonize GLP-2 activity in vivo, and a pharmaceutically acceptable carrier.

The GLP-2 antagonist activity of the present GLP-2 antagonists is manifest in vivo as a reduction in the mass of small bowel tissue or as an ability to inhibit the intestinotrophic activity of GLP-2 or intestinotrophic analogs thereof. Accordingly, there is provided, in another aspect of the invention, a method for reducing the mass or suppressing the proliferation of small bowel tissue in a patient, which comprises the step of delivering to that patient an amount of a GLP-2 antagonist of the invention effective to cause a reduction in the mass of small bowel tissue.

Patients for whom such treatment would be useful include those suffering from hyperplastic conditions of the small intestine, for example, as a result of GLP-2 overdose or of GLP-2 overproducing tumors, and conditions wherein prophylactic inducement of small bowel hypoplasia would be useful, for example, in the treatment of clinical obesity as a non-surgical alternative to resection of the small intestine.

IV. DETAILED DESCRIPTION OF THE INVENTION

The present invention relates to therapeutic and related uses of a novel class of GLP-2 antagonists, particularly for decreasing the growth rate of gastrointestinal tissue, most particularly small bowel. The biological effect of the present GLP-2 antagonists manifests as a decrease in small bowel weight, relative to a mock treated control or as an ability to inhibit the intestinotrophic activity of GLP-2 or an intestinotrophic analog of GLP-2, relative to a control animal given either GLP-2 or an intestinotrophic analog of GLP-2 alone.

The present GLP-2 antagonists are structural analogs of the intestinotrophic GLP-2 peptides. GLP-2 peptides refers collectively to the various vertebrate forms of GLP-2 and to modified forms (characterized by at least one addition, deletion, substitution, and/or incorporation of an amino acid residue with a blocking group) of the GLP-2 analogs which still retain intestinotrophic activity. However, as described herein, certain site-specific alterations of these intestinotrophic GLP-2 peptides can confer antagonist activity to the site-specifically altered analog.

Without being limited by following explanation, it is believed that the site specific alterations which confer antagonist activity interfere with one of the functional activities of the GLP-2 hormone peptide, but not all functional activities. For example, an alteration conferring antagonist activity to a GLP-2 analog may be one which does not inhibit hormone binding to its cognate receptor, but does prevent the subsequent signal transduction through the bound receptor. For example, the site specific alteration of the hormone may prevent dimerization of the hormone receptor which is necessary to transmit a signal to the interior of the cell. Such a mechanism for antagonistic activity has been observed with other hormones such as, for example, human growth hormone (see Fuh et al., Science, 1992, 256:1677-1680).

Generally, sites which are highly conserved among mammalian GLP-2's are candidates for modification in order to obtain an antagonist. Among mammals, at least residues 1–5, 7, 15, and 22, 29 and 32–33 are highly conserved. Therefore, deletion or substitution of the residues at these sites may result in a GLP-2 antagonist. Additionally, certain modifications of sites near these conserved sites may also cause antagonist activity by disrupting local tertiary amino acid structure or placement of the adjacent conserved residues.

The GLP-2 antagonists of the invention include peptide derivatives with a sequence derived from a vertebrate GLP-2 in that one or more of any of the first four N-terminal amino acids (relative to the sequence of human GLP-2) are deleted. These analogs are referred to herein as the deletion class of GLP-2 antagonists. From the deletion class of GLP-2 antagonists, it will be appreciated that GLP-2 antagonism can result from disruption of the N-terminal structure of GLP-2 within the first four amino acids. Thus, the deletion class of GLP-2 antagonists comprises: GLP-2(2-33), GLP-2(3-33), GLP-2(4-33) and GLP-2(5-33), [desAla$^2$]GLP-2, [desAsp$^3$]GLP-2 and [desGly$^4$]GLP-2.

Additionally, the GLP-2 antagonists of the invention include substitution derivatives of vertebrate GLP-2's. The substitution class of GLP-2 antagonists includes those antagonists which replace one of the following amino acids at the following positions (relative to sequence of the human GLP-2) with another amino acid: residues 15, 22, 29, 32, and 33. The substitution class of GLP-2 antagonists of the invention also includes a double substitution of both amino acid residues at position 5 and 7 with amino acids other than Serine. Also included in the substitution class are those incorporating certain Ala$^2$ substitutions.

It is to be understood that, in embodiments of the invention, the GLP-2 antagonists may incorporate any combination of a deletion and a substitution, or may incorporate two or more substitutions at the sites noted.

A. GLP-2 Antagonists

The GLP-2 antagonists may accordingly be analogs of human GLP-2 (SEQ ID NO:1), which has the following sequence:

```
His-Ala-Asp-Gly-Ser-Phe-Ser-Asp-Glu-Met-Asn-
1               5                  10

Thr-Ile-Leu-Asp-Asn-Leu-Ala-Ala-Arg-Asp-Phe-
            15                  20

Ile-Asn-Trp-Leu-Ile-Gln-Thr-Lys-Ile-Thr-Asp.
        25                  30      33
```

Unless otherwise specified, the term "GLP-2" refers to the sequence of human GLP-2.

The antagonists of the invention are polypeptides which comprise amino acid sequences corresponding to that of a first reference mammalian GLP-2 which has been mutated so that:
(i) from one to four of any of the first four N-terminal residues are deleted; or
(ii) at least one amino acid selected from the amino acid positions corresponding to the amino acid positions of human GLP-2 at Asp$^{15}$, Phe$^{22}$, Thr$^{29}$, Thr$^{32}$ and Asp$^{33}$ is substituted with an amino acid which does not naturally occur at that position in the reference GLP-2; or
(iii) both positions Ser$^5$ and Ser$^7$ are substituted;
(iv) position Ala$^2$ is substituted with an amino acid selected from the group consisting of Leu, Cys, Glu, Arg, Trp, and PO$_3$-Tyr$^2$; or
(v) a combination of (i), (ii), and/or (iii) is mutated.

In specific embodiments of the invention, for example, the GLP-2 antagonists of the invention which are altered at residue positions 1, 2, 3, 4, 5 and 7, 22, 29, 32, and/or 33 may be derivatives of rat GLP-2 which is an Ala$^{19}$ variant of human GLP-2; degu GLP-2, ox GLP-2, porcine GLP-2, guinea pig GLP-2 and hamster GLP-2, the sequences of which have been reported by many authors including Buhl et al in J. Biol. Chem., 1988, 263(18):8621.

GLP-2 residues which occur at a specific position are determined by aligning the sequences of GLP-2's isolated from different vertebrate species and comparing the sequence to the human sequence, reproduced above.

Further, the GLP-2 antagonists of the invention which are altered at residue positions 1, 2, 3, 4, 22, 29, 32, and/or 33, and/or a double substitution at positions 5 and 7, may be derivatives of GLP-2 agonists such as are described in co-pending U.S. application Ser. Nos. 08/632,533 and 08/631,273.

Amino acids substitutions appropriate at these sites to yield an antagonist can readily be determined using the murine model of GLP-2 antagonism herein described. That is, a GLP-2 compound incorporating a structural alteration is obtained and then screened in the murine model exemplified herein for GLP-2 antagonism activity. Those GLP-2 compounds which elicit a decrease in bowel growth and/or inhibit the intestinotrophic activity of GLP-2 or a GLP-2 agonist, are identified in this screen as GLP-2 antagonists.

GLP-2 antagonists of the present invention are considered to be functional antagonists of GLP-2 if, when assessed in the murine model exemplified herein, the agonist: (1) consistently mediates a measurable decrease in small bowel weight relative to a control animal receiving vehicle alone; and/or (2) when assessed by co-administration in said murine model with GLP-2 or a GLP-2 agonist (in a molar excess ratio of preferably 10:1, and more preferably 4:1 over agonist) results consistently in a measurable inhibition of the intestinotrophic effect of GLP-2 or the GLP-2 agonist, as revealed by a reduction in the increase in small bowel weight induced by GLP-2 administered alone.

Particularly suitable for therapeutic use are those functional antagonists of GLP-2 which mediate a bowel weight decrease of at least about 10% relative to a control animal receiving vehicle alone; preferred for therapeutic use are those which mediate a decrease in small bowel weight of at least 15% or more.

The small intestine mass reducing activity of the present GLP-2 antagonists is noted most significantly in relation to the jejunum, and particularly the proximal jejunum, and is also noted in the distal ileum. Additionally, the activity of GLP-2 antagonists may also be noted as a reduction in the crypt/villus height of the small intestine.

Alternatively, GLP-2 antagonists can be assessed using the co-administration model detailed above. In this case, antagonists are considered to be useful antagonists of GLP-2 if, when co-administered with GLP-2, or an intestinotrophic analog thereof, at a molar ratio of about 10:1, or more preferably at a molar ratio of about 4:1, they diminish the activity of GLP-2 or an intestinotrophic analog thereof by at least 10%, as manifest by a reduction in the increase in small bowel weight relative to a control animal treated with either GLP-2 or the GLP-2 agonist alone.

In another aspect of the invention, there is provided a method useful to identify antagonists of GLP-2, such as those described above, comprising the steps of:

1) obtaining a GLP-2 analog that incorporates an alteration within the peptide sequence:
2) treating a mammal with said analog using a regimen capable of eliciting a measurable loss of the mass of the intestine; and
3) determining the effect of said analog on small bowel weight and/or on the crypt/villus height of the crypt cells of the small intestine relative to a mock treated control animal, whereby a functional GLP-2 antagonist is identified as an analog of GLP-2 which elicits a decrease in said weight and/or said height.

In a related aspect of the invention, there is provided another method useful to identify functional GLP-2 antagonists comprising the steps of:

1) obtaining a GLP-2 analog which incorporates an alteration within the peptide sequence;;
2) treating a mammal with said analog in a regimen capable of inhibiting the intestinotrophic activity of GLP-2 or a GLP-2 agonist; and
3) determining the effect of said analog on small bowel weight and/or on the crypt/villus height of the crypt cells of the small intestine relative to a control animal given GLP-2 or a GLP-2 agonist, whereby said functional GLP-2 antagonist is identified as an analog of GLP-2 which inhibits the intestinotrophic activity of GLP-2 and/or the intestinotrophic activity of a GLP-2 agonist.

In a preferred version of the methods described above useful to identify functional GLP-2 antagonists, the GLP-2 analog is chosen from the GLP-2 antagonists described herein.

B. Choice of Substituting Amino Acids

The substituting amino acids can be chosen from the wide variety of amino acids available to peptide chemists, and include the D-amino acids as well as the L-amino acids and their numerous derivatives. Most practically, chosen amino acids will be amenable to incorporation by solid phase or solution phase synthesis, or by recombinant DNA production means.

In a first screen, analogs which are candidates for antagonistic activity are identified by alanine scanning mutagenesis or other systematic mutagenesis method. These alanine substitutions are tested for antagonistic activity using the methods described in detail herein.

In another aspect of the invention, more effective GLP-2 antagonists may then be made by drastically changing the character of the naturally occuring amino acid residue that is important in forming structural interactions (hydrogen bonding, salt bridging, hydrophobic interactions, positioning of residues) of the GLP-2 hormone with its target molecule (e.g. receptor). With this goal in mind, it is not normally necessary to screen each site with replacements by all 18 of the other naturally occurring residues. Instead, representative members of residue groups are selected. Generally, these groups are:

| a. positively charged residues: | His, Arg and Lys |
| b. negatively charged residues: | Asp and Glu |
| c. amides: | Asn and Gln |
| d. aromatic residues: | Phe, Tyr, Trp. |
| e. hydrophobic residues: | Ala, Pro, Gly, Val, Leu, Ile, and Met |
| f. uncharged hydrophilic residues: | Ser and Thr. |

When preparing these antagonist candidates, one would choose a residue from a group other than the type of residue which is naturally occuring at that position. Extreme substitutions are generated by selecting a residue from a group with opposed combinations of features. For example, a negatively charged residue may be substituted by a positively charged residue.

In the case of the $Ala^2$ substitutions, the substituting amino acids are selected carefully so that antagonists of GLP-2 activity result. It should be noted that substitutions at position 2 can have the effect of enhancing the intestinotrophic activity of GLP-2. For instance, when $Ala^2$ is replaced by Gly, the result is dramatically enhanced intestinotrophic activity as well as resistance to digestion of the GLP-2 peptide by DPP-IV enzyme. The GLP-2 antagonists of the present invention can surprisingly also be generated by substituting $Ala^2$. In embodiments of the invention, substituting amino acids at position 2 that are useful to generate GLP-2 antagonists are selected from Leu, Cys, Glu, Arg, Trp and $PO_3$-Tyr. GLP-2 antagonists incorporating these substitutions have the added advantage that they render the peptide resistant to digestion by DPP-IV enzyme. Preferably, the $Ala^2$ substituting amino acid is selected from Cys, Glu, Leu, and Arg.

Amino acids substituting for $Ser^5$ and $Ser^7$ are desirably selected independently from those incorporating a hydrophobic side chain such as Ala, as well as Gly and Val. Amino acids substituting for $Asp^{15}$, $Phe^{22}$, $Thr^{29}$, $Thr^{32}$, and $Asp^{33}$ are also desirably selected from those incorporating a small hydrophobic side chain, such as Ala, Gly and Val.

In embodiments of the invention, the substitution class of GLP-2 antagonists includes: $[Gly^2, Ala^{15}]$GLP-2, $[Ala^{15}]$GLP-2, $[Ala^{15}]$GLP-2(2-33), $[Ala^{15}]$GLP-2(3-33), $[Ala^{15}]$GLP-2(4-33), $[Ala^{15}]$GLP-2(5-33), $[Gly^2, Ala^{22}]$GLP-2, $[Gly^2, Ala^{29}]$GLP-2, $[Gly^2, Ala^{32}]$GLP-2, $[Gly^2, Ala^{33}]$GLP-2, $[Ala^5, Ala^7]$GLP-2, $[Ala^5, Ala^7]$GLP-2(2-33), $[Ala^5, Ala^7]$GLP-2(3-33), $[Ala^5, Ala^7]$GLP-2(4-33), $[Ala^5, Ala^7]$GLP-2(5-33), $[Ala^5]$GLP-2(2-33), $[Ala^5]$GLP-2(3-33), $[Ala^5]$GLP-2(4-33), $[Ala^5]$GLP-2(5-33), $[Ala^7]$GLP-2(5-33), $[Leu^2]$GLP-2, $[Glu^2]$GLP-2, $[Arg^2]$GLP-2, $[Trp^2]$GLP-2, $[PO_3$-$Tyr^2]$GLP-2, $[Cys^2]$GLP-2, $[Ala^7, Ala^{15}]$GLP-2, $[Ala^5, Ala^7, Ala^{15}]$GLP-2, $[Ala^5, Ala^{15}]$GLP-2(2-33), $[Ala^7, Ala^{15}]$GLP-2(2-33), and $[Ala^5, Ala^7, Ala^{15}]$GLP-2, $[Ala^{15}]$GLP-2, $[Ala^{29}]$GLP-2, $[Ala^{32}]$GLP-2 and $[Ala^{33}]$GLP-2.

C. Additional Modifications for Improving the Properties of the Analogs of the Invention The present GLP-2 antagonists, while incorporating a structural alteration of the type noted, may have various amino acid sequences consistent with the sequences of GLP-2 per se or of GLP-2 agonists. The GLP-2 antagonists may also be analogs of vertebrate GLP-2 agonists, in which collateral modifications have been made to enhance other biochemical, biological or physiological properties of the peptide. Such modifications include, for example (in those peptides for which antagonism is conferred by substitution other than at position 2), the substitution of native $Ala^2$ by an amino acid that renders the GLP-2 antagonist resistant to digestion by the enzyme DPP-IV. An amino acid suitable for this purpose includes particularly Gly. Also, the $Met^{10}$ residue can be replaced by an oxidatively more stable amino acid, such as Leu, Nle, Ile or Ala. Such Met[10]-substituted analogs are accordingly more stable during synthesis, work-up, and storage. Another modification in this context is replacement of the amino acid at position 20 by an amino acid other than Arg. In certain applications, particularly for the synthetic generation of pharmaceutically acceptable peptides, this modification is desirable to avoid the retention by the Arg residue of counterions from solvents such as TFA.

Within the scope of the present invention are also molecules in which the N- or C-terminus has been modified to incorporate a blocking group of the type used conventionally in the art of peptide chemistry to protect peptide termini from undesired biochemical attack and degradation in vivo. Suitable N-terminal protecting groups include, for example, $C_{1-5}$alkanoyl groups such as acetyl. Also suitable as N-terminal protecting groups are amino acid analogs lacking the amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched $C_{1-5}$alkyl groups, e.g., methyl, ethyl and propyl groups, while amide-forming groups include amino functions such as primary amine, or alkylamino functions, e.g., mono-$C_{1-5}$alkylamino and di-$C_{1-5}$alkylamino groups such as methylamino, ethylamino, dimethylamino, diethylamino, methylethylamino and the like. Amino acid analogs are also suitable for protecting the C-terminal end of the present compounds, for example, decarboxylated amino acid analogs such as agmatine.

Embodiments of the invention specifically include such analogs in which the N-terminal blocking group is acetyl; and analogs in which the C-terminal blocking group is an amine, e.g., —$NH_2$.

D. Synthesis of the GLP-2 Antagonists

The present GLP-2 antagonists can be synthesized using standard techniques of peptide chemistry and can be assessed for GLP-2 antagonist activity, all according to the guidance provided herein. Those GLP-2 antagonists that incorporate only L-amino acids can be produced in commercial quantities by application of recombinant DNA technology. For this purpose, DNA coding for the desired GLP-2 antagonist is incorporated into an expression vector and transformed into a microbial, e.g., yeast, or other cellular host, which is then cultured under conditions appropriate for GLP-2 antagonist expression. A variety of gene expression systems have been adapted for this purpose, and typically drive expression of the desired gene from expression regulatory elements used naturally by the chosen host. Because GLP-2 does not require post translational glycosylation for its activity, its production may conveniently be achieved in bacterial hosts such as *E. coli*. For such production, DNA coding for the selected GLP-2 antagonist may usefully be placed under expression controls of the lac, trp or PL genes of *E. coli*. As an alternative to expression of DNA coding for the GLP-2 antagonist per se, the host can be adapted to express GLP-2 antagonist as a fusion protein in which the GLP-2 antagonist is linked releasably to a carrier protein that facilitates isolation and stability of the expression product.

In an approach universally applicable to the production of selected GLP-2 antagonists, and one used necessarily to produce GLP-2 antagonist forms that incorporate non-genetically encoded amino acids and N- and C-terminally derivatized forms, the well established techniques of automated peptide synthesis are employed, general descriptions of which appear, for example, in J. M. Stewart and J. D. Young, *Solid Phase Peptide Synthesis*, 2nd Edition, 1984, Pierce Chemical Company, Rockford, Ill.; and in M. Bodanszky and A. Bodanszky, *The Practice of Peptide Synthesis*, 1984, Springer-Verlag, New York; Applied Biosystems 430A Users Manual, 1987, ABI Inc., Foster City, Calif. In these techniques, the GLP-2 antagonist is grown from its C-terminal, resin-conjugated residue by the sequential addition of appropriately protected amino acids, using either the Fmoc or tBoc protocols, as described for instance by Orskov et al, 1989, supra.

For the incorporation of N- and/or C- protecting groups protocols conventional to solid phase peptide synthesis methods can also be applied. For incorporation of C-terminal protecting groups, for example, synthesis of the desired peptide is typically performed using, as solid phase, a supporting resin that has been chemically modified so that cleavage from the resin results in a peptide having the desired C-terminal protecting group. To provide peptides in which the C-terminus bears a primary amino protecting group, for instance, synthesis is performed using a p-methylbenzhydrylamine (MBHA) resin so that, when peptide synthesis is completed, treatment with hydrofluoric acid releases the desired C-terminally aminated peptide. Similarly, incorporation of an N-methylamine protecting group at the C-terminus is achieved using N-methylaminoethyl-derivatized DVB resin, which upon HF treatment releases peptide bearing an N-methylamidated C-terminus. Protection of the C-terminus by esterification can also be achieved using conventional procedures. This entails use of resin/blocking group combination that permits release of side-chain protected peptide from the resin, to allow for subsequent reaction with the desired alcohol, to form the ester function. FMOC protecting groups, in combination with DVB resin derivatized with methoxyalkoxy-benzyl alcohol or equivalent linker, can be used for this purpose, with cleavage from the support being effected by TFA in dichloromethane. Esterification of the suitably activated carboxyl function e.g. with DCC, can then proceed by addition of the desired alcohol, followed by deprotection and isolation of the esterified peptide product.

Incorporation of N-terminal protecting groups can be achieved while the synthesized peptide is still attached to the resin, for instance by treatment with suitable anhydride and nitrile. To incorporate an acetyl protecting group at the N-terminus, for instance, the resin-coupled peptide can be treated with 20% acetic anhydride in acetonitrile. The N-protected peptide product can then be cleaved from the resin, deprotected and subsequently isolated.

Once the desired peptide sequence has been synthesized, cleaved from the resin and fully deprotected, the peptide is then purified to ensure the recovery of a single oligopeptide having the selected amino acid sequence. Purification can be achieved using any of the standard approaches, which include reversed-phase high-pressure liquid chromatography (RP-HPLC) on alkylated silica columns, e.g. $C_4$-, $C_8$-, or $C_{18}$-silica. Such column fractionation is generally accomplished by running linear gradients, e.g. 10–90%, of increasing % organic solvent, e.g. acetonitrile, in aqueous buffer, usually containing a small amount (e.g. 0.1%) of pairing agent such as TFA or TEA. Alternatively, ion-exchange HPLC can be employed to separate peptide species on the basis of their charge characteristics. Column fractions are collected, and those containing peptide of the desired/required purity are optionally pooled. In one embodiment of the invention, the peptide is then treated in the established manner to exchange the cleavage acid (e.g. TFA) with a pharmaceutically acceptable acid, such as acetic, hydrochloric, phosphoric, maleic, tartaric, succinic and the like, to provide a water soluble salt of the peptide.

E. Uses of the GLP-2 Antagonists of the Invention

According to the present invention, the GLP-2 antagonist is administered to treat patients that would benefit from decreased gastrointestinal tissue growth rate. In one aspect, patient candidates are those who would benefit from decreased mass of small intestine tissue. The effects of GLP-2 antagonists on this tissue, as evidenced by the results exemplified herein, is dramatic and would clearly benefit those patients suffering from diseases or conditions marked by hyperplasia in the small intestinal tract mucosa, which include GLP-2 producing tumors. Another group of patients who would clearly benefit from the effects of GLP-2 antagonists are those in whom it would be useful to induce hypoplasia of small intestine tissue, for example, patients who will in the near future be receiving radiotherapy or chemotherapy or patients who are receiving radiotherapy or chemotherapy. Small intestine epithelial cells are characterized by rapid cell division and are thus particularly susceptible to damage by radiotherapy or chemotherapy. Indeed, cell damage to the small intestinal epithelial cells is the cause of significant mortality and morbidity in cancer patients undergoing therapy. Thus, it would be desirable to slow the growth rate of these cells immediately prior to initiation of these therapies and during the course of the treatment. The ability to decrease the growth rate of small intestine cells in these patients, and thus achieve bowel rest prior to treatment with chemotherapy or radiotherapy, would have the additional benefit of allowing higher doses of radiotherapeutic and chemotherapeutic agents.

Another clinical situation wherein a functional antagonist of GLP-2 would be clinically useful is the treatment of a patient who has been chronically or acutely overdosed with GLP-2 or a GLP-2 agonist. Yet another potential application of functional antagonists of GLP-2 is to block transport of toxins or other drugs across the mucosal layer. Pathogenic effects in some diseases arise as a result of absorption of toxins or drugs via the intestinal epithelium. Elimination of the absorptive capacity of the small bowel by reducing the intestinal epithelium may be beneficial. For example, some diseases such as cholera are lethal because cholera toxin binds to receptors in the intestinal epithelium itself, leading to dehydration and death. GLP-2 antagonists may produce bowel rest, eliminating the target tissue for the toxin (intestinal epithelium) and hence the pathological response to cholera.

Yet another group of patients who would benefit from a decrease in the mass of the small intestine are those suffering from obesity, as a alternative to surgical intervention such as resection of the small intestine.

Thus, in one aspect the invention provides a method for causing a decrease in the proliferation of small bowel tissue in a patient in need thereof, comprising the step of delivering to the patient an amount of a GLP-2 antagonist of the present invention effective to antagonize GLP-2. The therapeutic efficacy of the GLP-2 antagonist treatment may be monitored by enteric biopsy to examine the villus morphology or by biochemical assessment of nutrient absorption. Additionally, efficacy may be assessed using a clinical endpoint relevant to the particular condition treated, for example, weight loss. In a related aspect the invention provides a method of treating a patient suffering from a gastrointestinal disease, by administering a therapeutically effective amount of a functional antagonist of the present invention, together with a pharmaceutically acceptable carrier, in order to reduce a pathological symptom of the gastrointestinal disease. For example, patients with small bowel cancer may be administered GLP-2 antagonist to decrease the size of the tumor. Alternatively, patients with bowel motility disorders, irritable bowel, and chronic diarrhea may benefit from GLP-2 antagonist to increase motility and/or reduce diarrhea.

In another of its aspects, the invention provides a method for treatment of patients to reduce gastrointestinal tissue mass as part of regimen involving radiotherapy or chemotherapy, in which there is administered to a patient a small bowel mass reducing amount of the GLP-2 antagonist. The invention embraces both co-administration of the GLP-2 antagonist with the radiotherapeutic agent or the chemotherapeutic agent or alternatively administration of the GLP-2 antagonist so as to reduce the growth of small bowel tissue prior to initiation of the radiotherapy or chemotherapy. Appropriate dosing regimens for GLP-2 antagonists may determined by monitoring the subsequent reduction in intestinal damage and/or recovery time after radiotherapy or chemotherapy.

In a further aspect, the invention provides a method for treatment of obesity, which comprises administering to an obese patient an effective amount of a GLP-2 antagonist capable of antagonizing the effects of GLP-2, as evidenced by weight loss under controlled dietary intake conditions.

In another aspect, the invention provides a method of treatment of a patient suffering from a GLP-2 producing tumor which comprises administering to a patient in need thereof an effective amount of a GLP-2 antagonist capable of antagonizing the effects of GLP-2, as evidenced by decrease in size of the intestinal epithelium and small bowel mass over the treatment period.

Another use for antagonists of GLP-2 is as a therapy for correcting a fluid imbalance due to a malabsorption problem across the small intestine. The efficacy of the GLP-2 antagonist treatment is monitored by assessing stool volume, ICF and ECF volume, urine volume and osmolarity, blood pressure, and plasma electrolytes.

F. Formulations of the GLP-2 Antagonists

For administration to patients, the GLP-2 antagonists are provided, in one aspect of the invention, in pharmaceutically acceptable form (e.g., as a preparation that is sterile-filtered e.g. through a 0.22μ filter) and substantially pyrogen-free. Desirably, the GLP-2 antagonist to be formulated migrates as a single or individualized peak on HPLC, exhibits uniform and authentic amino acid composition and sequence upon analysis thereof, and otherwise meets standards set by the various national bodies which regulate quality of pharmaceutical products.

For therapeutic use, the chosen GLP-2 antagonist is formulated with a carrier that is pharmaceutically acceptable and is appropriate for delivering the peptide by the chosen route of administration. Suitable pharmaceutically acceptable carriers are those used conventionally with peptide-based drugs, such as diluents, excipients and the like. Reference may be made to "Remington's Pharmaceutical Sciences", 17th Ed., Mack Publishing Company, Easton, Pa., 1985, for guidance on drug formulations generally. In one embodiment of the invention, the compounds are formulated for administration by infusion or by injection, either subcutaneously or intravenously, and are accordingly utilized as aqueous solutions in sterile and pyrogen-free form and optionally buffered to a slightly acidic or physiological pH. Thus, the compounds may be administered in distilled water or, more desirably, in saline, buffered saline or 5% dextrose solution. Water solubility may be enhanced, if desired, by incorporating a solubility enhancer, such as acetic acid.

The aqueous carrier or vehicle can be supplemented for use as injectables with an amount of gelatin that serves to depot the GLP-2 antagonist at or near the site of injection, for its slow release to the desired site of action. Concentrations of gelatin effective to achieve the depot effect are expected to lie in the range from 10–20%. Alternative gelling agents, such as hyaluronic acid, may also be useful as depoting agents.

The GLP-2 antagonists of the invention may also be formulated as a slow release implantation device for extended and sustained administration of GLP-2 antagonist. Examples of such sustained release formulations include composites of biocompatible polymers, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., *Polymers for Advanced Technologies* 3:279–292 (1992). Additional guidance in selecting and using polymers in pharmaceutical formulations can be found in the text by M. Chasin and R. Langer (eds.), "Biodegradable Polymers as Drug Delivery Systems," Vol. 45 of "Drugs and the Pharmaceutical Sciences," M. Dekker, New York, 1990. Liposomes may also be used to provide for the sustained release of a GLP-2 antagonist. Details concerning how to use and make liposomal formulations of drugs of interest can be found in, among other places, U.S. Pat. No. 4,944,948; U.S. Pat. No. 5,008,050; U.S. Pat. No. 4,921,706; U.S. Pat. No. 4,927,637; U.S. Pat. No. 4,452,747; U.S. Pat. No. 4,016,100; U.S. Pat. No. 4,311,712; U.S. Pat. No. 4,370,349; U.S. Pat. No. 4,372,949; U.S. Pat. No. 4,529,561; U.S. Pat. No. 5,009,956; U.S. Pat. No. 4,725,442; U.S. Pat. No. 4,737,323; U.S. Pat. No. 4,920,016. Sustained release formulations are of particular interest when it is desirable to provide a high local concentration of a GLP-2 antagonist or prolonged circulating levels.

The GLP-2 antagonist can be utilized in the form of a sterile-filled vial or ampoule, that contains an amount of the peptide effective to antagonize endogenous GLP-2 activity, in either unit dose or multi-dose amounts. The vial or ampoule may contain the GLP-2 antagonist and the desired carrier, as an administration-ready formulation. Alternatively, the vial or ampoule may contain the GLP-2 peptide in a form, such as a lyophilized form, suitable for reconstitution in a suitable carrier, such as phosphate-buffered saline.

As an alternative to injectable formulations, the GLP-2 antagonist may be formulated for administration by other routes. Oral dosage forms, such as tablets, capsules and the like, can be formulated in accordance with standard pharmaceutical practice.

Finally, chronic delivery of the GLP-2 antagonist for weight loss or other therapeutic indications may be achieved through gene therapy techniques. For example, cells may be engineered ex vivo to express high levels of the GLP-2 antagonist, and then such cells may be implanted into the patient for therapeutic efficacy.

G. Dosages of the GLP-2 Antagonists of the Invention

The therapeutic dosing and regimen most appropriate for patient treatment will of course vary with the disease or condition to be treated, and according to the patient's weight and other parameters. The results presented hereinbelow demonstrate that a dose of GLP-2 antagonist equivalent to about 1 mg/kg to 100 μg/kg (or less) administered twice daily over 10 days can generate very significant decrease in small bowel mass. It is conceivable that much smaller doses, e.g., in the μg/kg range, and shorter or longer duration or frequency of treatment, will also produce therapeutically useful results, i.e., a statistically significant decrease particularly in small bowel mass. The dosage sizes and dosing regimen most appropriate for human use are guided by the results herein presented, and can be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Primary among these is the amount of GLP-2 normally circulating in the plasma, which is on the order of 151 pmol/ml in the resting state, rising to 225 pmol/ml after nutrient ingestion for healthy adult humans (Orskov, C. and Holst, J. J., 1987, Scand. J. Clin. Lav. Invest. 47:165). Additional factors include the size of the patient, the age of the patient, the general condition of the patient, the particular disease being treated, the severity of the disease, the presence of other drugs in the patient, the in vivo activity of the GLP-2 antagonist and the like. The trial dosages would be chosen after consideration of the results of animal studies and the clinical literature. It will be appreciated by the person of ordinary skill in the art that information such as binding constants and Ki derived from in vitro GLP-2 binding competition assays may also be used in calculating dosages, as well as the calculated half-life of the GLP-2 antagonist in vivo.

A typical human dose of a GLP-2 antagonist would be from about 10 μg/kg body weight/day to about 10 mg/kg/day, preferably from about 50 μg/kg/day to about 5 mg/kg/day, and most preferably about 100 μg/kg/day to 1 mg/kg/day. As it is conceivable that the GLP-2 antagonists of the invention could be up to 10 to even 100 times more potent than GLP-2, a typical dose of such a GLP-2 antagonist may be lower, for example, from about 100 ng/kg body weight/day to 1 mg/kg/day, preferably 1 μg/kg/day to 500 μg/kg/day, and even more preferably 1 μg/kg/day to 100 μg/kg/day.

EXAMPLE 1—GLP-2 Antagonist Synthesis

The following GLP-2 antagonist peptides were synthesized:

[Gly$^2$, Ala$^{15}$]GLP-2; [Gly$^2$, Ala$^{22}$]GLP-2; [Gly$^2$, Ala$^{29}$]GLP-2; [Gly$^2$, Ala$^{32}$]GLP-2; [Gly$^2$, Ala$^{33}$]GLP-2; ratGLP-2(2-33); ratGLP-2(3-33); ratGLP-2(4-33); ratGLP-2(5-33); [Leu$^2$]GLP-2; [Glu$^2$]GLP-2; [Arg$^2$]GLP-2; [Trp$^2$]GLP-2; [Cys$^2$]GLP-2; [PO$_3$-Tyr$^2$]GLP-2; and [Phg$^2$]GLP-2.

Solid phase peptide synthesis (SPPS) was carried out manually in a 300 milliliter (ml) vessel on a 3 millimole (mmole) scale using 6 grams (g) of chloromethyl (Merrifield) resin (for C-terminal free acid peptides) with a substitution of 0.5 milliequivalents (meq) per gram. Amino acids were protected at the amino-terminus with the t-butyloxycarbonyl (tBoc) group. The side-chains of trifunctional amino acids were protected with the benzyl (Bz, for serine and threonine), benzyloxymethyl (BOM, for histidine), 2-bromobenzyloxycarbonyl (2-BrZ, for tyrosine), 2-chlorobenzyloxycarbonyl (2-ClZ, for lysine), cyclohexyl (cHex, for aspartic and glutamic acids), and tosyl (Tos, for arginine) groups. The first amino acid was coupled to the chloromethyl resin through esterification of the protected amino acid in the presence of potassium fluoride (KF). C-terminal amide peptides were synthesized on a 4-methylbenzhydrylamine (MBHA) resin on a 3 mmol scale using 6 g of resin with a substitution of 0.5 meq/g. The first amino acid was coupled to the MBHA resin according to the procedure described for peptide elongation.

Amino-group deprotection was carried out using 50% trifluoroacetic acid (TFA) in dichloromethane (CH$_2$Cl$_2$), followed by neutralization using two washes of 10% triethylamine (Et$_3$N) in CH$_2$Cl$_2$. Peptide elongation was carried out using N,N-dicyclohexylcarbodiimide/1-hydroxybenzotriazole (DCC/HOBt) activation in CH$_2$Cl$_2$/dimethylformamide (DMF). The growing peptide chain was capped after each elongation step with 20% Ac$_2$O in CH$_2$Cl$_2$. The peptide-resin was washed after each elongation, capping and deprotection step with isopropanol (iPrOH) and methanol (MeOH). The washes were repeated once. N-terminal acetyl peptides were prepared by acetylation of the terminal amino-group with 20% Ac$_2$O in CH$_2$Cl$_2$ after deprotection and neutralization as described. Resin-bound products were routinely cleaved by a low-high procedure using hydrogen fluoride (HF) containing dimethyl-sulfide (DMS) and p-cresol as scavengers.

Crude peptides were purified by preparative high pressure liquid chromatography (HPLC) using a Vydac C18, 15–20 μm wide-pore, 2 inch×12 inch, reverse-phase silica column using gradient elution with 0.1t TFA in water modified with acetonitrile. Elution was monitored at 220 nanometers (nm). Each fraction collected was analyzed for purity by analytical HPLC using a Vydac C18, 5 μm, 4.6×254 millimeter (mm), reverse-phase silica column by gradient elution using 0.1% TFA in water modified with acetonitrile, and monitored at 215 nm. Fractions demonstrating greater than 95% purity were combined and lyophilized. Acetate salts of the peptides were prepared from the TFA salts by dissolution of the lyophilized powder in water, with addition of acetonitrile to aid in dissolution when necessary. The solution was passed through a protonated Bio-Rex-70 cation exchange resin. The resin was washed with 5 bed-volumes of water, and the resin-bound peptide eluted with 50% acetic acid in water. The eluent was diluted with water and lyophilized.

The final lyophilized powder was analyzed for purity by two analytical reverse-phase HPLC methods using a Vydac C18, 5 μm, 4.6×254 mm reverse-phase silica column. Two solvent systems were used: a gradient of water adjusted to pH 2.25 with triethylamine phosphate, modified with acetonitrile; and a gradient of 0.1% TFA in water, modified with acetonitrile. The column eluent was monitored at 215 nm. The identity of each product was confirmed by amino acid analysis and by electrocopy-mass spectroscopy.

The GLP-2 antagonists were next formulated as described below in Example 2. Each of the GLP-2 antagonists was fully soluble in water at room temperature unless otherwise noted.

EXAMPLE 2—GLP-2 Antagonist Formulation

The GLP-2 antagonists were formulated for injection either in phosphate buffered saline or as a gelatin-containing depot formulation. For the PBS-formulated GLP-2 antagonist preparations, a 10× stock PBS solution was first prepared, using 80 g NaCl (BDH ACS 783), 2 g KCl (BDH ACS 645), 11.5 g Na$_2$HPO$_4$ (Anachemia AC-8460), and 2 g KH$_2$PO$_4$ (Malinckrodt AR7100), which was brought to a total volume of one litre with sterile distilled water. The final working solution was obtained by 10:1 dilution of the stock solution with sterile distilled water and adjusted to pH 7.3–7.4 if necessary, using sufficient volumes of 10N Na OH. The working solution was then autoclaved for 30 minutes. In the final working PBS solution, concentrations were 137 mM NaCl, 2.7 mM KCl, 4.3 mM Na$_2$HPO$_4$.7H2O, and 1.4 mM KH$_2$PO$_4$.

The GLP-2 antagonists, as a powdered peptide, were added to the working PBS solution as required to generate formulations having the desired peptide concentrations. For example, to generate a PBS solution of GLP-2 antagonist at 130 mg/l, 5.2 mg of GLP-2 antagonist was dissolved in 40 ml of PBS to yield a GLP-2 antagonist concentration of 130 μg/ml, and filter sterilized. 0.5 ml of the GLP-2 antagonist solution was injected twice daily.

To generate the gelatin-based GLP-2 antagonist formulations, a gelatin solution was first prepared by dissolving 12 grams of gelatin (Sigma, G-8150 Lot #54HO7241 Type A from Porcine skin [9000-70-8] ~300 Bloom) in 100 ml distilled water. The gelatin solution was then autoclaved, warmed at 37° C., and the GLP-2 antagonist previously dissolved in phosphate buffered saline as described above was added to achieve specific, desired peptide concentrations. For instance, to generate a gelatin-based PBS solution of the GLP-2 antagonist at a concentration of 130 mg/l, 10 ml of a PBS solution prepared with 5.2 mg of GLP-2 antagonist was diluted with 30 ml of the 20% working gelatin solution as first described above. The solution was mixed by gentle pipeting, to yield a final solution of 130 mg/l GLP-2 antagonist in PBS/15% gelatin.

EXAMPLE 3—Assay for Resistance to Dipeptidyl Peptidase IV

The following peptides were tested for resistance to dipeptidyl peptidase IV (DPP-IV): a control peptide, ratGLP-2; the [D-Ala$^2$]ratGLP-2 agonist; and the [Gly2] ratGLP-2 agonist. Additionally, the following peptides were also tested for DPP-IV resistance: [Gly$^2$, Ala$^{15}$]GLP-2, [Gly$^2$, Ala$^{22}$]GLP-2, [Gly$^2$, Ala$^{29}$]GLP-2, [Gly$^2$, Ala$^{32}$]GLP-2, [Gly$^2$, Ala$^{33}$] GLP-2, [Leu$^2$]GLP-2, [Glu$^2$]GLP-2, [Arg$^2$ ]GLP-2, [Trp$^2$][PO$_3$-Tyr$^2$]GLP-2, and [Cys$^2$]GLP-2. To perform the assay, 2.5 microliters (μl) of a solution of human placental DPP-IV (Calbiochem, La Jolla, Calif., cat. #317624) containing 0.125 milliunits (mU) of enzyme in 50% glycerol, 10 mM Tris, pH 7.8, EDTA and 0.02% NaN$_3$ was added to 50 μl of a solution of the test peptide prepared at a concentration of 0.2 mg/ml in PBS at pH 7.4. The mixture was incubated at 37° C. in a circulating water bath for 24 hours. The incubation was quenched by the addition of 50 μl of a solution of diprotin A prepared at a concentration of 4 mg/ml in PBS. Each peptide was tested in duplicate.

Each sample was analyzed by reverse-phase (RP) HPLC as follows: 90 μl of the quenched incubation mixture was injected onto a Rainin Dynamax 300 Å, C18, 5 micron, 4.6×250 millimeter column. The samples were eluted with 0.1% trifluoroacetic acid (TFA) in water modified with 0.1% acetonitrile using a linear gradient and a flow rate of 1 ml per minute. Sample components were detected at 214 nanometers (nm). The extent of cleavage was measured by relative integration of the peak corresponding to the cleavage product compared to that of the remaining undigested parent peptide. The cleavage product of the control peptide, ratGLP-2(1-33), which should be ratGLP-2(3-33), was confirmed to have resulted from cleavage between residues Ala$^2$ and Asp$^3$ by comparison of the retention time of this component to that of a synthetic peptide standard, ratGLP-2(3-33), and by collection of the product from the HPLC and analysis by mass spectrometry.

After the 24 hour incubation, 22% of the control peptide, ratGLP-2, was cleaved by DPP-IV. No cleavage products were detected for the peptides [D-Ala$^2$]ratGLP-2, [Gly$^2$] ratGLP-2, [Gly$^2$, Alal$^5$]GLP-2, [Gly$^2$, Ala$^{22}$]GLP-2, [Gly$^2$, Ala$^{29}$]GLP-2, [Gly$^2$, Ala$^{32}$]GLP-2, [Gly$^2$, Ala$^{33}$]GLP-2, [Leu$^2$]GLP-2, [Glu$^2$] GLP-2, [Arg$^2$]GLP-2, [Trp$^2$]GLP-2, [PO$_3$-Tyr$^2$]GLP-2, and [Cys$^2$]GLP-2 after 24 hours.

EXAMPLE 4—GLP-2 Antagonist Assessment by Administration into Mice

Recipients were CD1 mice obtained from Charles River Laboratory (Ontario, Canada). The CD1 mice were aged-matched females at time of injection (n=3–4 per group), 6 weeks of age, unless otherwise specified. The animals were allowed a minimum of 24 hours to acclimatize to the laboratory facility before the initiation of each experiment. Animals were identified by ear punch. The mice were not restricted by diet or activity during the experiments. The light/dark cycle was 12 hours, between 6 pm to 6 am. Controls were age- and sex-matched (n=3–4) animals. Mice were injected subcutaneously, twice a day (b.i.d.), with 2.5 µg peptide in a total volume of 0.5 cc of PBS and were monitored daily in the laboratory facility. Animals were sacrificed 10 or 14 days after injection, and were fasted at least 20 hours before sacrifice.

The mice were anaesthetized with $CO_2$ and exsanguinated by cardiac puncture. Blood was collected in 75 µl of TED (Trasysol; EDTA (5000 KIU/ml: 1.2 mg/ml; Diprotin-A), and the blood was centrifuged at 14 k×g for 5 minutes and the plasma was stored at −70° prior to analysis. The small bowel was removed from the peritoneal cavity, from pylorus to cecum, cleaned weighed and measured. For comparative purpose, sections from each animal were obtained from the identical anatomical position. Fragments each measuring 1.5–2.0 cm in length were obtained 8±2 cm, 18±2 cm, 32±2 cm from pylorus for histomorphometry representing proximal jejunum, distal jejunum and distal ileum. Each small bowel fragment was opened longitudinally on its antimesenteric border in a tissue block and then placed on 10% formalin (vol./vol.) overnight, then transferred to 70% ETOH.

Percentage change in small bowel weight was calculated by dividing the mean change in bowel weight of antagonist treated mice, relative to mice treated with vehicle only, by the mean bowel weight of mice treated with vehicle only, and multiplying this figure by 100.

TABLE 1

| GLP-2 antagonist | % Decrease in Small Bowel Weight |
|---|---|
| [$Gly^2$, $Ala^{15}$]GLP-2 | 14 |
| [$Gly^2$, $Ala^{22}$]GLP-2 | 8 |
| [$Gly^2$, $Ala^{29}$]GLP-2 | 19 |
| [$Gly^2$, $Ala^{32}$]GLP-2 | 17 |
| [$Gly^2$, $Ala^{33}$]GLP-2 | 6 |
| [$Leu^2$]GLP-2 | 23 |
| [$Glu^2$]GLP-2 | 25 |
| [$Arg^2$]GLP-2 | 23 |
| [$Trp^2$]GLP-2 | 5 |
| [$Cys^2$]GLP-2 | 20 |
| [$PO_3$-$Tyr^2$]GLP-2 | 6 |
| [$Phg^2$]GLP-2 | 2 |

These results establish that antagonists of human GLP-2 which contain substitutions of the conserved residues at positions 15, 29, 32, or 33 with an alanine residue will actually cause a decrease in small bowel weight when injected into mice. In contrast, analogs of human GLP-2 which contain a wild type residue at these positions (but which do contain the $Gly^2$ substitution) will increase small bowel weight when injected into mice using an identical experimental protocol (data not shown). Therefore, we conclude that substitution of the residues at positions 15, 29, 32, or 33 partially disrupts GLP-2 functional activity and results in a GLP-2 antagonist.

Additionally, this data also shows the extremely surprising result that substitutions of the $Ala^2$ position with an amino acid residue other than Gly, specifically Leu, Glu, Arg, Trp, Cys, $PO_3$-Tyr, and Phg, resulted in antagonistic activity.

EXAMPLE 5—GLP-2 Antagonist Assessment by Co-administration into Mice with GLP-2

The candidate peptide antagonist and rat GLP-2 were dissolved in PBS to give a final ratio of 25 µg antagonist/2.5 µg GLP-2 per 0.5 ml phosphate buffered saline solution (for a 10:1 ratio), or 12.5 µg antagonist/2.5 µg GLP-2 per 0.5 ml phosphate buffered saline solution (for a 4:1 ratio), as indicated. The antagonist/GLP-2 mixture was administered to 6–8 week old CD1 female mice subcutaneously, with the amount of peptide injected being 25 µg antagonist/2.5 µg GLP-2 in 0.5 ml twice a day, or 12.5 µg antagonist/2.5 µg GLP-2 in 0.5 ml twice a day. After 10–14 days, peptide-injected and control (saline-injected) mice were sacrificed, and small bowel weights were determined.

TABLE 2

| # | GLP-2 antagonist | % Antagonism | Ratio of Antagonist to GLP-2 administered [by Weight] |
|---|---|---|---|
| 1 | ratGLP-2(2-33) | 42 | 10:1 |
| 2 | ratGLP-2(3-33) | 33 | 4:1 |
| 3 | ratGLP-2(4-33) | 32 | 10:1 |
| 4 | ratGLP-2(5-33) | 16 | 10:1 |

These results illustrate that deletions of the first one to four residues of GLP-2 results in an antagonist which will antagonize the intestinotrophic activity of rat GLP-2 when co-injected into experimental mice. These results are significant for at least two reasons. First, this data reveals that the extreme amino terminus of the GLP-2 peptides is involved in the intestinotrophic effect of GLP-2. Therefore, other alterations which disrupt this terminus, for example, substitutions of amino acids with opposite properties, instead of deletions, will likely also convey antagonistic activity to the resulting analog. Second, co-administration of antagonist and GLP-2 will serve to decrease or even eliminate the intestinotrophic effect of GLP-2. Antagonists of GLP-2 may therefore be administered to a subject in situations where excess production of GLP-2 occurs, for example, a patient with a tumor which secretes GLP-2 and/or responds trophically to GLP-2 peptide.

INCORPORATION BY REFERENCE

All patents, patents applications, and publications cited are incorporated herein by reference.

EQUIVALENTS

The foregoing written specification is sufficient to enable one skilled in the art to practice the invention. Indeed, various modifications of the above-described means for carrying out the invention which are obvious to those skilled in the field of molecular biology, protein chemistry, medicine or related fields are intended to be within the scope of the following claims.

What is claimed is:

1. A polypeptide consisting of an amino acid sequence of a mammalian GLP-2 mutated so that: (i) from one to four of any of the first four N-terminal residues are deleted; or (ii) at least one amino acid selected from the amino acid positions corresponding to the amino acid positions of human GLP-2 at Asp$^{15}$, Phe$^{22}$, Thr$^{29}$, Thr$^{32}$ and Asp$^{33}$ is substituted with an amino acid which does not naturally occur at that position in the mammalian GLP-2; or (iii) both positions Ser$^5$ and Ser$^7$ are substituted independently with any amino acid other than Ser; (iv) position Ala$^2$ is substituted with an amino acid selected from the group consisting of Leu, Cys, Glu, Arg, Trp, and PO$_3$-Tyr$^2$; or (v) the polypeptide contains a combination of two or more of the substitutions or deletions described in (i), (ii), and (iii); said polypeptide exhibiting GLP-2 antagonist activity.

2. The peptide as defined in claim 1, wherein the mammalian GLP-2 is selected from the group consisting of human GLP-2, degu GLP-2, ox GLP-2, porcine GLP-2, guinea pig GLP-2 and hamster GLP-2.

3. The peptide as defined in claim 2, wherein the mammalian GLP-2 is human GLP-2.

4. The peptide as defined in claim 1, said peptide having a substitution at a position selected from the group consisting of Asp$^{15}$, Phe$^{22}$, Thr$^{29}$, Thr$^{32}$, and Asp$^{33}$.

5. The peptide as defined in claim 1, said peptide having a substitution at both positions Ser$^5$ and Ser$^7$.

6. The peptide as defined in claim 1, said peptide selected from the group consisting of [Leu$^2$]GLP-2, [Glu$^2$]GLP-2, [Arg$^2$]GLP-2, [Trp$^2$]GLP-2, [PO$_3$-Tyr$^2$]GLP-2, and [Cys$^2$]GLP-2.

7. The peptide as defined in claim 1, which is GLP-2(2-33).

8. The peptide as defined in claim 1, which is GLP-2(3-33).

9. The peptide as defined in claim 1, which is GLP-2(4-33).

10. The peptide as defined in claim 1, which is GLP-2(5-33).

11. The peptide as defined in claim 1, which peptide further comprises one or more substitutions selected from the group consisting of: (i) substitution of Ala$^2$ with Val, Gly, or D-Ala; (ii) substitution of Met$^{10}$ with Leu, Ile, Nle, or Ala; (iii) an amino terminal blocking group; and (iv) a carboxy terminal blocking group.

12. The peptide as defined in claim 4, selected from the group consisting of: [Gly2,Ala$^{15}$]GLP-2; [Gly$^2$, Ala$^{22}$]GLP-2; [Gly$^2$, Ala$^{29}$]GLP-2; [Gly$^2$, Ala$^{32}$]GLP-2; and [Gly$^2$, Ala$^{33}$]GLP-2.

13. The pharmaceutical composition comprising a therapeutically effective amount of a peptide according to claim 1, and a pharmaceutically acceptable carrier.

14. A host cell transformed with a polynucleotide expression construct which encodes a polypeptide according to claim 1.

15. A mutated mammalian GLP-2 polypeptide exhibiting GLP-2 antagonist activity selected from the group consisting of: [Gly$^2$, Ala$^{15}$]GLP-2, [Ala$^{15}$]GLP-2, [Ala$^5$]GLP-2(2-33), [Ala$^{15}$]GLP-2(3-33), [Ala$^{15}$]GLP-2(4-33), [Ala$^{15}$]GLP-2(5-33), [Gly$^2$, Ala$^{22}$]GLP-2, [Gly$^2$, Ala$^{29}$]GLP-2, [Gly$^2$, Ala$^{32}$]GLP-2, [Gly$^2$Ala$^{33}$]GLP-2, [Ala$^5$, Ala$^7$]GLP-2, [Ala$^5$, Ala$^7$]GLP-2(2-33), [Ala$^5$, Ala$^7$]GLP-2(3-33), [Ala$^5$, Ala$^7$]GLP-2(4-33), [Ala$^5$, Ala$^7$]GLP-2(5-33), [Ala$^5$]GLP-2(2-33), [Ala$^5$]GLP-2(3-33), [Ala$^5$]GLP-2(4-33), [Ala$^5$]GLP-2(5-33), [Ala$^7$]GLP-2(5-33), [Leu$^2$]GLP-2, [Glu$^2$]GLP-2, [Arg$^2$]GLP-2, [Trp$^2$]GLP-2, [PO$_3$-Tyr$^2$]GLP-2, [Cys$^2$]GLP-2, [Ala$^7$, Ala$^{15}$]GLP-2, [Ala$^5$, Ala$^7$, Ala$^{15}$]GLP-2, [Ala$^5$, Ala$^{15}$]GLP-2(2-33), [Ala$^7$, Ala$^{15}$]GLP-2(2-33), and [Ala$^5$, Ala$^7$, Ala$^{15}$]GLP-2, [Ala$^{15}$]GLP-2, [Ala$^{29}$]GLP-2, [Ala$^{32}$]GLP-2, and [Ala$^{33}$]GLP-2.

* * * * *